United States Patent [19]

Bloomfield, III

[11] Patent Number: 4,726,066

[45] Date of Patent: Feb. 16, 1988

[54] INTER-ORAL SPEECH AID

[75] Inventor: John W. Bloomfield, III, Hilton Head Island, S.C.

[73] Assignee: P. O. Vox Medical, Inc., Hilton Head Island, S.C.

[21] Appl. No.: 886,511

[22] Filed: Jul. 15, 1986

Related U.S. Application Data

[63] Continuation-in-part of Ser. No. 802,585, Nov. 26, 1985, Pat. No. 4,691,360.

[51] Int. Cl.⁴ .............................................. G10L 5/00
[52] U.S. Cl. ........................................ 381/53; 381/70
[58] Field of Search ...................................... 381/53, 70

[56] References Cited

U.S. PATENT DOCUMENTS 3,084,221  4/1963  Cooper .................................. 381/70
4,338,488  7/1982  Lennox ................................. 381/70

Primary Examiner—Emanuel S. Kemeny
Attorney, Agent, or Firm—Fleit, Jacobson, Cohen & Price

[57] ABSTRACT

A touch switch contacts on a unit housing are bridged by the fingers of a person's hand when holding the housing to trigger operation of a signal generating oscillator driving a transducer from which "voice" sound is generated and transmitted through a sound tube into the person's mouth for articulation of speech. The oscillator is operated at a low duty cycle for moderate battery consumption when the sound tube is extended from a retracted storage position within a recess formed in the housing.

14 Claims, 4 Drawing Figures

INTER-ORAL SPEECH AID

This invention relates to electronic voice sound synthesis and more particularly to a device for simulating the acoustical output of the human larynx such as that disclosed in my prior copending application, Ser. No. 802,585, filed Nov. 26, 1985, now U.S. Pat. No. 4,691,360, filed 9/1/87, with respect to which the present application is a continuation-in-part.

BACKGROUND OF THE INVENTION

Voice synthesizing devices which enable articulation of speech on an interim or permanent basis, utilizing an external source of sound, are most useful for post operative care of patients in hospitals where vocal communication is difficult or impossible. Providing such patients with a disposable, portable and battery operated unit from which the "voice" sound is generated, calls for an effective but economical unit which will be easy to use and safe in oxygen enriched atmospheres often found in hospitals.

It is therefore an important object of the present invention to provide a safe and low cost voice synthesizer unit which is useful for post operative care of patients, especially in environments with high ambient noise.

SUMMARY OF THE INVENTION

In accordance with the present invention an electronic synthesizer has a housing dimensioned to be grasped between the fingers and thumb of one hand by a patient to thereby bridge a pair of elements on the housing which form the skin contacts of a touch switch. A circuit is completed through the patient's body between the contact elements in series with protective current limiting circuitry to produce a signal processed by a current controlling detection device from which an output is obtained to trigger a signal generating oscillator through load isolating means as long as the touch switch circuit is completed. A battery voltage source continuously powers the signal generating oscillator through a switch that is opened to turn off the oscillator whenever a sound tube transmitting the acoustical output of the transducer is in its retracted position within a recess formed in the housing. The circuit associated with the signal generating oscillator features means for operation thereof at an adjusted frequency and a low duty cycle having a constant on-time phase of less than 50% to minimize power consumption from the battery.

As a result of the foregoing features of the voice synthesizer, safe generation of "voice" sound is electronically produced from the transducer, the sound being transmitted through the extended sound tube inserted into the patient's oral cavity. The moderated battery power consumption, as aforementioned, provides a relatively long useful life for the unit between battery replacements.

BRIEF DESCRIPTION OF DRAWING FIGURES

DETAILED DESCRIPTION OF PREFERRED EMBODIMENT

Figure 1:
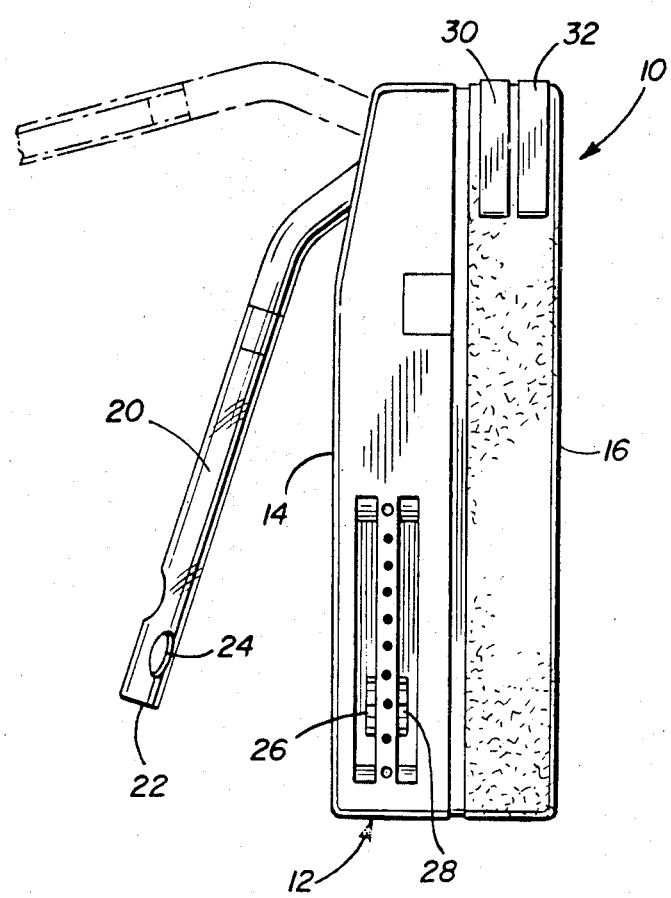
FIG. 1 is a side elevation view of the device of the present invention in accordance with one embodiment.
Figure 2:
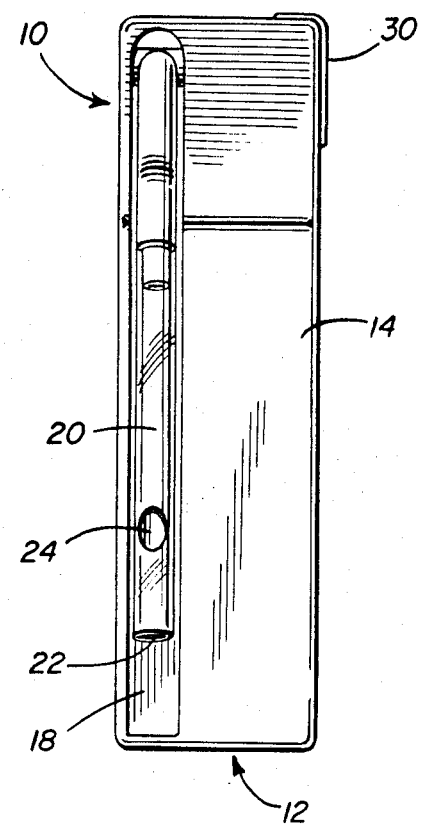
FIG. 2 is a front elevation view of the device shown in FIG. 1.

Referring now to the drawings in detail, FIGS. 1 and 2 illustrate a typical sound generating unit constructed in accordance with the present invention, generally referred to by reference numeral 10. The unit is enclosed by a generally elongated, rectangular housing 12 having a front face portion 14 and a removable rear portion 16. The front face portion is formed with a recess 18 into which an elongated conduit or sound tube 20 is retracted to a storage position. The sound tube is pivotally mounted within the housing for displacement from the retracted position to extended positions as shown in FIG. 1 in dotted and solid lines. The outer end 22 of the sound tube is open and adjacent to such open end the tube is formed with additional openings 24 from which sound is emitted.

The front face portion 14 of the housing is provided on one side with adjustable volume and pitch controls 26 and 28 of the slider type. The rear portion 16 of the housing is made of an electrically non-conductive material from which a pair of closely spaced touch contact plate elements 30 and 32 project preferably at one end of the housing. These contact elements are adapted to be readily bridged electrically by light tactile skin pressure of the fingers of one hand holding the housing between such fingers and the thumb. An electrical circuit is thereby completed through the body of a person to activate the unit.

Figure 3:
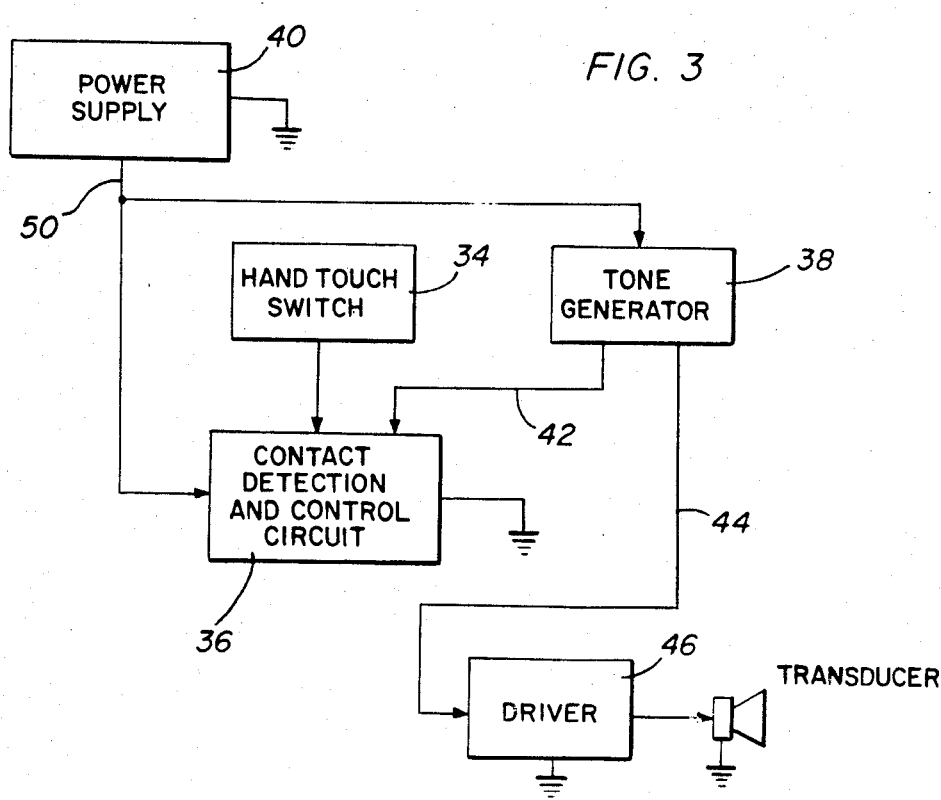
FIG. 3 is a schematic block diagram showing the general functional arrangement of the device illustrated in FIGS. 1 and 2.

The skin contact elements 30 and 32 form a hand touch switch 34 as diagrammed in FIG. 3 controlling a contact detection and control circuit 36 through which a tone generator 38 is triggered into operation. The tone generator 38 and circuit 36 are powered by a battery associated with a power supply 40. Power consumption by the tone generator is controlled by the detection and control circuit 36 through a grounding line 42, limiting operation to periods during which the contact elements of the hand switch 34 are bridged. The output of the tone generator is transmitted through line 44 to a transducer driver 46.

Figure 4:
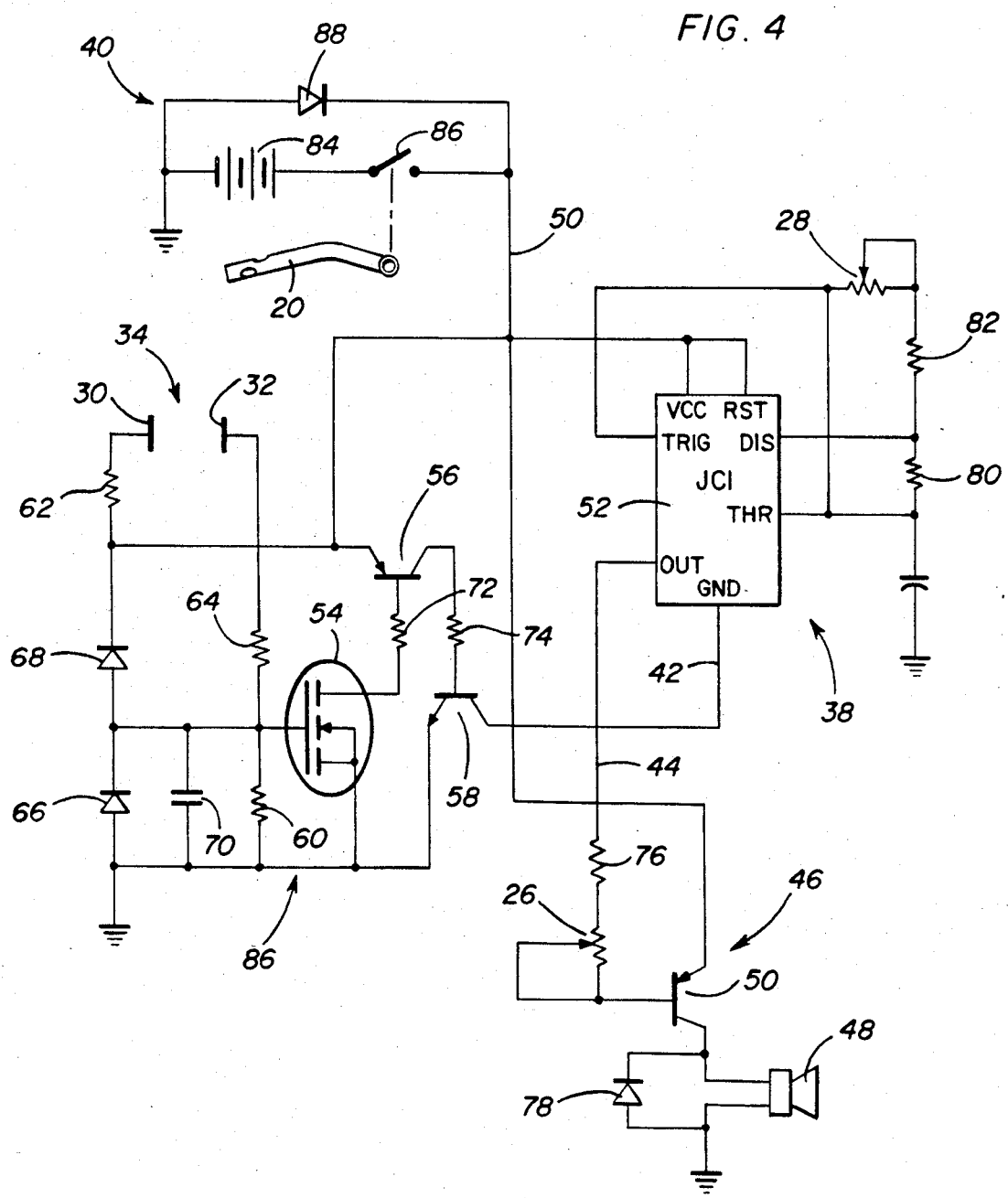
FIG. 4 is a detailed circuit diagram corresponding to the arrangement depicted in FIG. 3.

The circuitry associated with the voice sound generating system diagrammed in FIG. 3, is specifically illustrated in FIG. 4 showing the driver circuit 46 connected to ground through a sound emitting speaker or transducer 48. The driver circuit includes a transistor 50 forming an emitter-collector circuit connected in series with the transducer 48 between a dc voltage line 50 from the power supply 40 to ground. The voltage line 50 is also connected to the power and reset terminals of an integrated circuit chip 52 of the tone generator 38 and to the hand touch switch 34 through the contact detection and control circuit 36. The detection portion of circuit 36 features an N-channel enhanced isolated gate MOS field effect transistor 54 which detects bridging of the touch contact elements 30 and 32 of the hand touch switch 34 to supply a triggering signal through a load isolating buffer transistor 56 to a control transistor 58 connected by line 42 to the ground terminal of the circuit chip 52 in order to activate the tone generator. The output terminal of the circuit chip 52 is connected by line 44 to the driver circuit 46 as aforementioned.

The "voice" sound emitted from unit 10 enters the extend sound tube 20 within the housing 12 and travels through the tube to its open end 22. With the open end of the tube in the mouth, speech may be formed from such externally generated "voice" sound as it is done with respect to natural "voice" sound generated by the human larynx. The generation of sound occurs in response to operation of the tone generating circuit 38 when it is activated through line 42 by the contact detection and control circuit 36 detecting circuit closing of the hand touch switch 34.

The field effect transistor 54 of the detection and control circuit 38 is normally held in a non-conductive state by resistor 60 connecting its input gate to ground. When the touch plate elements 30 and 32 are shorted by a person's fingers, current is conducted through the person's body from the positive voltage line 50 to the input gate in series with resistors 62 and 64, thereby raising the input gate voltage to a turn-on level of approximately 8 volts, for example. The transistor 54 is thus rendered conductive in a safe manner by the current limiting action of resistors 62 and 64 providing high static voltage protection. The diodes 66 and 68 respectively connecting the input gate to ground and to the voltage line 50, prevent any static discharge from exceeding the gate voltage limits for damage free operation of the transistor 54. The capacitor 70 connected between ground and the input gate, provides high pass filtering of the input signal to minimize false triggering in an electrically noisy environment.

The output of transistor 54 is connected by resistor 72 to the input base of transistor 56 in order to isolate the grounded electrodes of transistor 54 from any current loads thereby increasing the sensitivity of the transistor 54 to inputs from the touch switch 34. The transistor 56 acts as a buffer amplifier coupling the output of transistor 54 in series with resistor 74 to the input base of transistor 58 acting as a ground sink control for the ground terminal of the oscillator circuit chip 52 of the tone generator 38. The collector of sink control transistor 58 being connected to the ground terminal of the chip 52, floats high when the chip circuit is quiescent to effectively remove it from the power supply and disable its operation as an oscillator and buffer for the transducer 48.

The transducer 48 is driven by the driver transistor 46 at the low duty cycle of the tone generator 38 to which it is coupled by series connected resistor 76 and adjustable volume control resistor 26 interconnected between the input base of transistor 46 and line 44 to the output terminal of the oscillator chip 52. During operation, volume control adjustment of resistor 26 will affect the current drive at the base of transistor 50 and its saturation voltage to vary the voltage drop across the transducer 48. Any high induced current is blocked by diode 78 connected across the transducer.

Because of the low duty cycle of operation imposed on the driver 46 by the tone generator 38, it will be off usually 80% of the time to moderate dissipation of power. Such low duty cycle is set by the resistance ratio between resistor 80 and the series connected resistor 82 and the pitch control resistor 28 in circuit with the oscillator chip 52 forming an astable multivibrator generating the tone which drives the transducer at 75 Hz, for example. The on-time set by resistor 80 remains constant for all frequencies selected by adjustment of the pitch control resistor 28. A typical on-time for the duty cycle is 20%. The oscillator circuit is normally disconnected from the power supply by the non-conductive transistor 58 of the detection circuit 36 as aforementioned.

The power supply 40 is based on a standard 9 volt alkaline transistor battery 84 having its positive terminal connected through switch 86 to the voltage line 50. The switch 86 is mechanically coupled to the pivoted sound tube 20, as shown, so as to be maintained open as long as the sound tube is in its retracted storage position. A diode 88 connected across the battery and the switch 86 provides temporary protection against damage from incorrect reverse battery connections.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. In a voice synthesizing device having a source of voltage, a signal generator powered by said source, a transducer driven by the signal generator and a housing enclosing the source, the signal generator and the transducer, said housing being dimensioned for holding in the hand of a person, the improvement comprising a sound tube mounted in the housing and displaceable between retracted and extended positions relative to the housing, selectively operable switch means for disabling the signal generator in the retracted position of the sound tube and means responsive to current conductive through the hand in contact with the housing for triggering operation of the signal generator.

2. The improvement as defined in claim 1 wherein said current responsive means includes electrically conductive contact elements fixedly mounted on the housing in non-conductively spaced relation to each other and detection circuit means connected to the contact elements for sensing the current conducted therebetween through the hand.

3. The improvement as defined in claim 2 including load isolating means operatively connecting the current responsive means to the signal generator for enabling the signal generator.

4. The improvement as defined in claim 3 wherein said current responsive means further includes current limiting means operatively connecting the contact elements to the detection circuit means for preventing flow of excessive current between the contact elements.

5. The improvement as defined in claim 2 wherein said current responsive means includes current limiting means operatively connecting the contact elements to the detection circuit means for preventing flow of excessive current between the contact elements.

6. The improvement as defined in claim 1 including load isolating means operatively connecting the current responsive means to the signal generator for enabling the signal generator.

7. In a voice synthesizing device having a source of voltage, a signal generator powdered by said source, a transducer driven by the signal generator and a sound tube displaceable between retracted and extended positions, the improvement including means connected to signal generator for limiting operation thereof to a duty cycle having a constant on-time of less than 50% during which the signal generator is powered by the source, driver means operatively connecting the signal generator to the transducer for generating an output at an adjustable amplitude and disabling means responsive to displacement of the sound tube to the retracted position for disconnecting the source from the signal generator.

8. In an electronic artificial larynx having a tone generator, a signal generator connected to the tone generator and a hollow tube having one end connected to the tone generator and an opposite end for placement in the mouth of a human, the improvement comprising:
   (a) a housing dimensioned to fit within the hand of said human and enclosing the tone generator, the signal generator and said one end of the tube;
   (b) current detection means within the housing for opening and closing an electrical circuit that includes the signal generator;
   (c) a pair of spaced contacts fixedly attached to the housing, means coupling said contacts to the current detection means for closing the circuit including the signal generator in response to current conducted through the hand in engagement with the contacts; and
   (d) means connecting said one end of the tube to the housing for extension of the tube from a retracted position within the housing to expose the opposite end for said placement into the mouth.

9. The artificial larynx of claim 8, including switch means actuated by said extension of the tube for enabling the tone generator.

10. The improvement as defined in claim 8 wherein said housing is formed with a recess within which the tube is seated in the retracted position of the conduit means.

11. A voice simulating device having a source of voltage, means connected to said source for generating a signal characteristic of the acoustical wave form produced by a human larnyx, transducer means for reproducing said signal as an audible tone, driver means for connecting said signal generating means to the transducer means and conduit means for transmitting the audible tone from the transducer means into a human oral cavity wherein the tone is adapted to be transposed into intelligible speech, the improvement comprising a housing enclosing the voltage source, the signal generating means, the transducer means and the driver means, touch means fixedly mounted on the housing for contact by fingers of a person, and current detection means responsive to said contact of the touch means for enabling the signal generating means.

12. The improvement as defined in claim 11 wherein said signal generating means includes an oscillator circuit having a circuit completing ground terminal connected to the detection responsive means.

13. An apparatus for operating a tone generator of an electronic artificial larynx comprising:
   (a) a housing dimensioned to fit within a human hand and enclosing the tone generator therein;
   (b) electronic switch means actuated within the housing for operating the tone generator; and
   (c) touch means conducting current to the switch means for actuation thereof, including a pair of fixedly spaced contacts on the housing between which said current is conducted through the human hand to actuate said switch means and said tone generator.

14. The apparatus of claim 13 including signal generating means connected to the tone generator for operation thereof in response to said actuation of the switch means, a source of electrical energy for powering the signal generating means and means connected to the signal generating means for limiting operation thereof to a duty cycle having an on-time phase of less than 50% of the duty cycle.

* * * * *